(12) United States Patent
Lee

(10) Patent No.: US 6,727,276 B2
(45) Date of Patent: Apr. 27, 2004

(54) EPOTHILONE DERIVATIVES FOR THE TREATMENT OF REFRACTORY TUMORS

(75) Inventor: Francis Y. F. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/071,988

(22) Filed: Feb. 8, 2002

(65) Prior Publication Data

US 2002/0165257 A1 Nov. 7, 2002

Related U.S. Application Data

(60) Provisional application No. 60/269,858, filed on Feb. 20, 2001.

(51) Int. Cl.$^7$ .................... A61K 31/335; A61K 31/425

(52) U.S. Cl. ...................... 514/450; 514/449; 514/365

(58) Field of Search ............................... 514/449, 450, 514/365

(56) References Cited

U.S. PATENT DOCUMENTS

| | | | |
|---|---|---|---|
| 5,969,145 A | 10/1999 | Schinzer et al. |
| 6,194,181 B1 | 2/2001 | Hofmann et al. |
| 6,204,388 B1 | 3/2001 | Danishefsky et al. |
| 6,211,412 B1 | 4/2001 | Georg et al. |
| 6,242,469 B1 | 6/2001 | Danishefsky et al. |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | WQ009967252 | * 12/1999 |
| WO | 00/00485 | 1/2000 |
| WO | 00/31247 | 6/2000 |
| WO | 00/37473 | 6/2000 |
| WO | 00/49021 | 8/2000 |
| WO | WO00/050423 | * 8/2000 |
| WO | 00/66589 | 11/2000 |

OTHER PUBLICATIONS

Balog, A., et al., "Total Synthesis of (–)–Epothilone A", Angew. Chem. Int. Ed. Engl., vol. 35, No. 23/24, 2801–2803 (1996).

Bertini, F., et al., "Alkenes from Epoxides by Reductive Elimination with Magnesium Bromide–Magnesium Amalgam", Chem. Commun., 144 (1970).

Bollag, D.M., et al., "Epothilones, A New Class of Microtubule–stabilizing Agents with a Taxol–like Mechanism of Action", Cancer Res. 55, No. 11, 2325–2333 (1995).

Fujisawa, T., et al., "Deoxygenation of Epoxides to Olefins with $FeCl_3$—n–BuLi System", Chem. Lett., 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", J. Org. Chem., vol. 43, No. 12, 2477–2479 (1978).

(List continued on next page.)

Primary Examiner—Theodore J. Criares
(74) Attorney, Agent, or Firm—Rena Patel; Anastasia P. Winslow

(57) ABSTRACT

A method of treating tumors in a mammal, especially a human that have demonstrated resistance to oncology with taxane oncology agents is disclosed. The method is effective where the tumor has initially been unresponsive to taxane therapy or has developed resistance during the course of treatment. The method comprising the administration of an epothilone derivative selected from those represented by formula I:

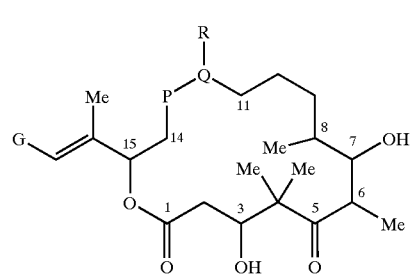

The subject epothilone derivatives are advantageous in addition to their enhanced potency and effectiveness against tumors that have demonstrated resistance to therapy with taxane oncology agents in that both are efficacious upon oral administration.

20 Claims, 5 Drawing Sheets

OTHER PUBLICATIONS

Gladysz, J. A., et al., "Deoxygenation of Epoxides by Metal Atom Cocondensation", *J. Org. Chem.*, vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium (TiCl$_3$/LiAlH$_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et. al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium (NbCl$_5$/NaAlH$_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1982).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epthilone A", *Bioorg. Med. Chem. Letts.*, vol. 6., No. 7, 893–898 (1996).

Winkler, J. D., et al., "A Model For The Taxol (Paclitaxel)/ Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1 / 2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1996).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantionselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)–Epothilone A", *Chem. Eur. J.*, vol. 5, No. 9, 2483–2491 (1999).

Schinzer, D., et al., "Syntheses of (–)–Epothilone B", *Chem. Eur. J.*, vol. 5, No. 9, 2492–2500 (1999).

Nicolaou, K. C., et al., "Synthesis and Biological Properties of C12,13–Cyclopropylepothilone A and Related Epothilones", *Chemistry & Biology*, vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84–87 (1998).

Nicolaou et al., "Total Synthesis of Oxazole– and Cyclopropane–Containing Epothilone B Analogues by the Macrolactonization Approach", Chemistry, European Journal, vol. 3, No. 12, 1971–1986 (1997).

Nicolaou et al., "Chemical Biology of Epothilones", Angew. Chem. Int. Ed., 37, 2014–2045 (1988).

* cited by examiner

Figure 1. Cytotoxicity spectrum of BMS-310705 versus a panel of eight tumor cell lines). Bar graphs, on the right, depict the $IC_{50}$ values of the cell lines listed on the left hand column (top to bottom).

Figure 2. (A) Comparative antitumor activity of IV BMS-310705 and IV BMS-247550 in the Pat-7 human ovarian carcinoma model. Compound was administered at the indicated doses, every 4 days for a total of 3 administrations starting 10 days after tumor implantation Q4D x3;10). Each datum point represents the median tumor weight of 8 mice. (B) Dose-response relationship for BMS-310705 in the Pat-7 tumor model.

Figure 3. Comparative antitumor activity of oral BMS-310705 and IV BMS-247550 versus the A2780Tax human ovarian carcinoma model. Compound was administered at the indicated doses, every 4 days for a total of 3 administrations starting 13 days after tumor implantation Q4D x3;13). Each datum point represents the median tumor weight of 8 mice.

Figure 4. Comparative antitumor activity of oral BMS-310705 and IV BMS-247550 in the Pat-7 human ovarian carcinoma model. Compound was administered at the indicated doses, every 4 days for a total of 3 administrations starting 10 days after tumor implantation Q4D x3;10). Each datum point represents the median tumor weight of 8 mice.

EPOTHILONE DERIVATIVES FOR THE TREATMENT OF REFRACTORY TUMORS

CROSS-REFERENCE TO RELATED APPLICATION

This application claims priority from provisional application serial No. 60/269,858, filed Feb. 20, 2001, incorporated herein by reference in its entirety.

FIELD OF THE INVENTION

The present invention relates to the use of certain potent epothilone analogs in the treatment of tumors that have demonstrated resistance to therapy with other chemotherapeutic agents.

BACKGROUND OF THE INVENTION

Epothilones are macrolide compounds that find utility in the pharmaceutical field. For example, epothilones A and B having the structures:

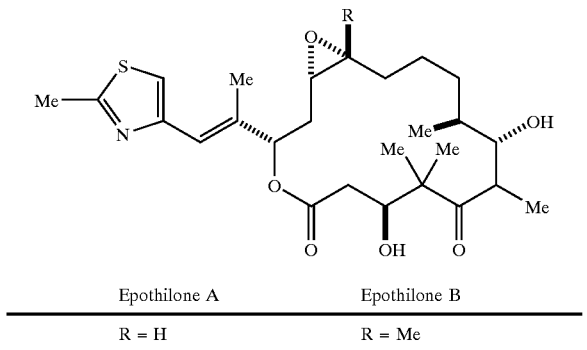

| Epothilone A | Epothilone B |
|---|---|
| R = H | R = Me | may be found to exert microtubule-stabilizing effects similar to paclitaxel (TAXOL®) and hence cytotoxic activity against rapidly proliferating cells, such as tumor cells or other hyperproliferative cellular disease, see Hofle et al., *Angew. Chem. Int. Ed. Engl.*, Vol. 35, No.13/14, 1567–1569 (1996); WO93/10121 published May 27, 1993; and WO97/19086 published May 29, 1997.

Derivatives and analogs of epothilones A and B have been synthesized and may be used to treat a variety of cancers and other abnormal proliferative diseases. Such analogs are disclosed in Hofle et al., *Id.; Nicolaou* et al., *Angew. Chem. Int. Ed. Engl.*, Vol. 36, No. 19, 2097–2103 (1997); and Su et al., *Angew. Chem. Int. Ed. Engl.*, Vol. 36, No. 19, 2093–2097 (1997). In some instances, epothilone derivatives have demonstrated enhanced properties over the original epothilones A and B. The present invention is concerned with the discovery that two such epothilone derivatives may be utilized to treat certain cancers that have demonstrated resistance to other chemotherapeutic agents, such as oncolytic agents of the taxane family of compounds.

SUMMARY OF THE INVENTION

In accordance with the present invention, tumors demonstrating a clinical resistance to treatment with taxane oncology agents may be treated with an epothilone derivative selected from those represented by formula I:

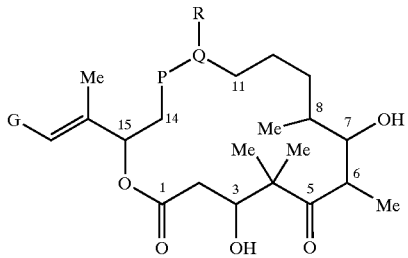

wherein G, P, Q and R have the meanings given below. The compounds represented by formula I have previously demonstrated significantly enhanced potency over other known chemotherapeutic agents, for example, epothilones A and B above and certain others including those in the taxane series. The compounds represented by formula I are further advantageous in that, unlike most oncology agents, they are efficacious via oral administration.

DETAILED DESCRIPTION OF THE INVENTION

Figure 1:
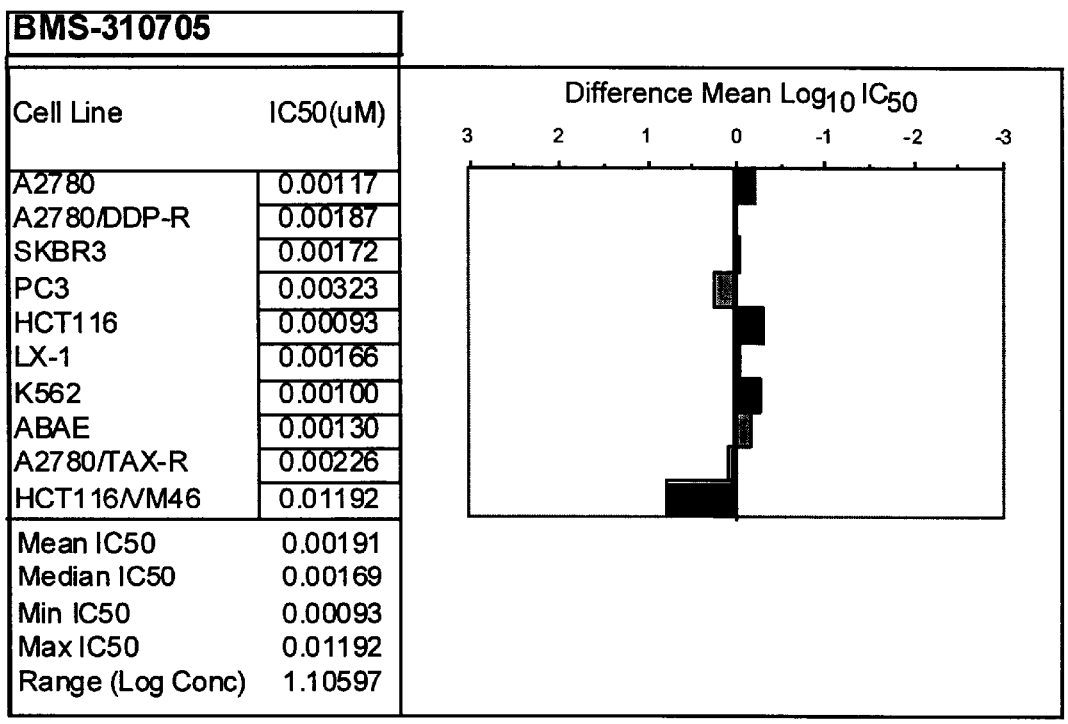
FIG. 1 is a bar graph showing the cytotoxicity spectrum of a compound of the invention.

Processes of the present invention provide advantageous treatment for tumors that have demonstrated resistance to treatment with chemotherapeutic agents, such as those of the taxane family. The term "resistance to treatment" as utilized herein includes both tumors that are initially unresponsive to treatment with a chemotherapeutic agent as well as tumors that are initially responsive, but develop resistance over the course of treatment. Compounds useful in the subject method are epothilones, a class of oncology agents. The subject epothilone derivatives are represented by formula I:

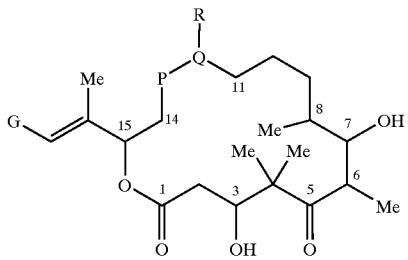

wherein:
P—Q is a carbon-carbon double bond or an epoxide;
G is

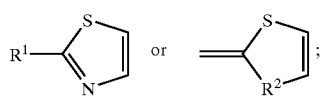

R is selected from the group consisting of H, alkyl, and substituted alkyl;

R¹ is selected from the group consisting of

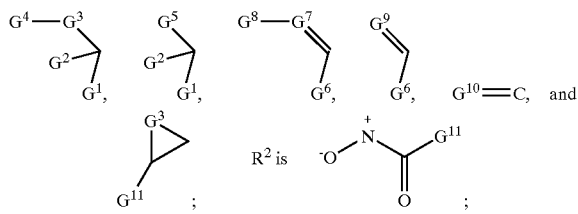

G¹ is selected from the group consisting of H, halogen, CN, alkyl and substituted alkyl;

G² is selected from the group consisting of H, alkyl, and substituted alkyl;

G³ is selected from the group consisting of O, S, and NZ¹;

G⁴ is selected from the group consisting of H, alkyl, substituted alkyl, OZ², NZ²Z³, Z²C=O, Z⁴SO₂, and optionally substituted glycosyl;

G⁵ is selected from the group consisting of halogen, N₃, NCS, SH, CN, NC, N(Z¹)₃⁺ and heteroaryl;

G⁶ is selected from the group consisting of H, alkyl, substituted alkyl, CF₃, OZ⁵, SZ⁵, and NZ⁵Z⁶;

G⁷ is CZ⁷ or N;

G⁸ is selected from the group consisting of H, halogen, alkyl, substituted alkyl, OZ¹⁰, SZ¹⁰, NZ¹⁰Z¹¹;

G⁹ is selected from the group consisting of O, S, —NH—NH— and —N=N—;

G¹⁰ is N or CZ¹²;

G¹¹ is selected from the group consisting of H₂N, substituted H₂N, alkyl, substituted alkyl, aryl, and substituted aryl;

each Z¹, Z⁶, Z⁹, and Z¹¹ is, independently, selected from the group consisting of H, alkyl, substituted alkyl, acyl, and substituted acyl;

Z² is selected from the group consisting of H, alkyl, substituted alkyl, aryl, substituted aryl, and heterocyclyl;

each Z³, Z⁵, Z⁸, and Z¹⁰ is, independently, selected from the group consisting of H, alkyl, substituted alkyl, acyl, substituted acyl, aryl, and substituted aryl;

Z⁴ is selected from the group consisting of alkyl, substituted alkyl, aryl, substituted aryl, and heterocyclyl;

Z⁷ is selected from the group consisting of H, halogen, alkyl, substituted alkyl, aryl, substituted aryl, OZ⁸, SZ⁸, and NZ⁸Z⁹; and Z¹² is selected from the group consisting of H, halogen, akyl, substituted alkyl, aryl, and substituted aryl;

with the proviso that when R¹ is

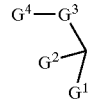

G¹, G², G³ and G⁴ cannot simultaneously have the following meanings:
G¹ and G² is H, G³ is O and G⁴ is H or Z²C=O wherein Z² is an alkyl group, and pharmaceutically acceptable salts thereof and any hydrates, solvates or geometric, optical and stereoisomers thereof.

Preferred compounds in accordance with the present invention are those represented by formula Ia:

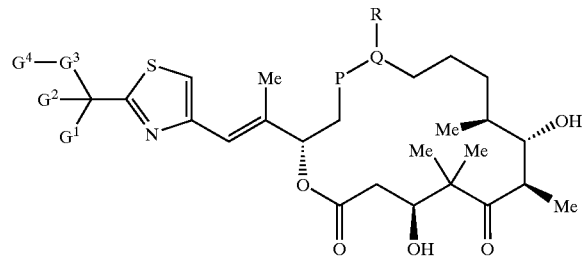

Ia wherein:
P—Q is a carbon-carbon double bond or an epoxide;
R is H or a methyl group;
G¹ is H, an alkyl group, a substituted alkyl group or a halogen atom;
G² is H, an alkyl group or a substituted alkyl group;
G³ is an O atom, an S atom or an NZ¹ group;
Z¹ is H, an alkyl group, a substituted alkyl group, an acyl group, or a substituted acyl group;
G⁴ is H, an alkyl group, a substituted alkyl group, an OZ² group, an NZ²Z³ group, a Z²C=O group, a Z⁴SO₂ group or an optionally substituted glycosyl group;
Z² is H, an alkyl group, a substituted alkyl group, an aryl group, a substituted aryl group or a heterocyclic group;
Z³ is H, an alkyl group, a substituted alkyl group, an acyl group or a substituted acyl group; and
Z⁴ is an alkyl, a substituted alkyl, an aryl, a substituted aryl or a heterocyclic group,
with the proviso that G¹, G², G³ and G⁴ cannot simultaneously have the following meanings:
G¹ and G² is H, G³ is O, and G⁴ is H or Z²C=O wherein Z² is an alkyl group.

A further preferred group of compounds in accordance with the present invention is represented by formula Ib:

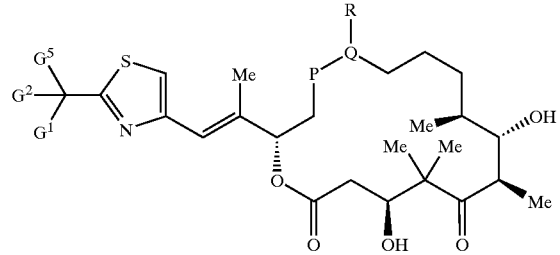

Ib wherein:
P—Q is a carbon-carbon double bond or an epoxide;
R is H or a methyl group;
G¹ is H, an alkyl group, a substituted alkyl group or a halogen atom;
G² is H, an alkyl group or a substituted alkyl group; and
G⁵ is a halogen atom, an N₃ group, an NCS group, an SH group, a CN group, an NC group or a heterocyclic group.

Another preferred group of compounds in accordance with the present invention is represented by the formula IIa:

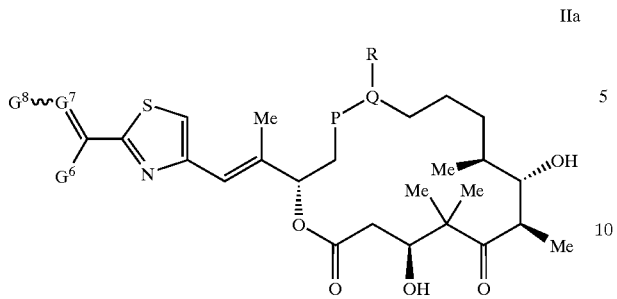

IIa

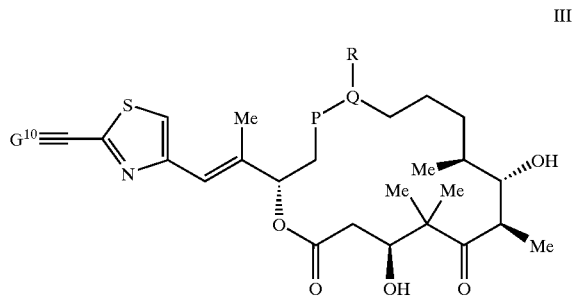

III wherein:
P—Q is a carbon-carbon double bond or an epoxide;
R is H or a methyl group;
$G^6$ is H, an alkyl group, a substituted alkyl group or a $CF_3$, $OZ^5$, $SZ^5$ or $NZ^5Z^6$ group;
$Z^5$ is H, an alkyl group, a substituted alkyl group, an acyl group or a substituted acyl group;
$Z^6$ is H, an alkyl group or a substituted alkyl group;
$G^7$ is a $CZ^7$ group or an N atom;
$Z^7$ is H, halogen atom, an alkyl group, a substituted alkyl group, an aryl group, or a substituted aryl group, or an $OZ^8$, $SZ^8$ or $NZ^8Z^9$ group;
$Z^8$ is H, an alkyl group, a substituted alkyl group, an acyl group or a substituted acyl group;
$Z^9$ is H, an alkyl group or a substituted alkyl group;
$G^8$ is H, a halogen atom, an alkyl group, a substituted alkyl group, or an $OZ^{10}$, $SZ^{10}$ or $NZ^{10}Z^{11}$ group;
$Z^{10}$ is H, an alkyl group, a substituted alkyl group, an acyl group, a substituted acyl group, an aryl group, or a substituted aryl group; and
$Z^{11}$ is H, an alkyl group, a substituted alkyl group, an acyl group, or a substituted acyl group.

Another group of preferred compounds within the scope of the present invention is represented by formula IIb:

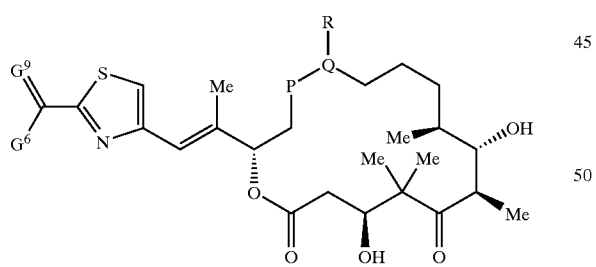

IIb wherein:
P—Q is a carbon-carbon double bond or an epoxide;
R is H or a methyl group;
$G^6$ is H, an alkyl group, a substituted alkyl group or a $CF_3$, $OZ^5$, $SZ^5$ or $NZ^5Z^6$ group;
$Z^5$ is H, an alkyl group, a substituted alkyl group, an acyl group or a substituted acyl group;
$Z^6$ is H, an alkyl group or a substituted alkyl group; and
$G^9$ is an O or S atom or an —N=N— group.

Another preferred group of compounds in accordance with the present invention is represented by the formula III:

wherein:
P—Q is a carbon-carbon double bond or an epoxide;
R is H or a methyl group;
$G^{10}$ is an N atom or a $CZ^{12}$ group; and
$Z^{12}$ is H, a halogen atom, an alkyl group, a substituted alkyl group, an aryl group, or a substituted aryl group.

An additional preferred group of compounds in accordance with the present invention is represented by the formula IV:

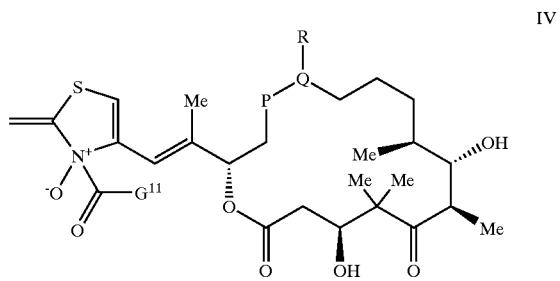

IV wherein:
P—Q is a carbon-carbon double bond or an epoxide;
R is H or a methyl group; and
$G^{11}$ is an $H_2N$ group, a substituted $H_2N$ group, an alkyl group, a substituted alkyl group, an aryl group or a substituted aryl group.

A particularly preferred group of compounds in accordance with the present invention is represented below:

[1S-[1R*,3R*(E),7R*,10S*,11R*,12R*,16S*]]-3-[2-[2-(azidomethyl)-4-thiazolyl]-1-methylethenyl]-7,11-dihydroxy-8,8,10,12,16-pentamethyl-4,17-dioxabicyclo-[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-(2-aminomethyl-4-thiazolyl)ethenyl]-4,17-dioxabicyclo[14.1.0]heptadecane-5,9-dione;

[1S-[1R*,3R*(E),7R*,10S*,11R*,12R*,16S*]]-3-[2-[2-[[[(1,1-dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-[[[(1,1-dimethylethoxy)carbonyl]amino]methyl]-4-thiazolyl]-1-methyl-ethenyl]-4,8-dihydroxy-5,5,7,9,13-pentamethyl-1-oxa-13(Z)-cyclohexadecene-2,6-dione;

[4S-[4R*,7S*,8R*,9R*,15R*(E)]]-16-[2-[2-(aminomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-dihydroxy-8,8,10,12-tetramethyl-3-[1-methyl-2-[2-

[(pentanoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(3-acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide;

[1S-[1R*,3R*(E),7R*,10S*,11R*,12R*,16S*]]-7,11-dihydroxy-3-[2-[2-(methoxymethyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-(phenoxymethyl)-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[(ethylthio)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(ethoxymethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(2,3,4,6-tetraacetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(2',3',4',6'-tetraacetyl-beta-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(6'-acetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(p-toluenesulfonyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-(bromomethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(5-bromo-2-methyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-[2-(cyanomethyl)-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-(cyanomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-dihydroxy-3-[2-[2-(1H-imidazol-1-ylmethyl)-4-thiazolyl]-1-methylethenyl]-8,8,10,12-pentamethyl-4,17-dioxabicyclo[14.1.0]heptadecane-5,9-dione;

[1S-[1R*,3R*(E),7R*,10S*,11R*,12R*,16S*]]-3-[2-(2-formyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-formyl-4-thiazolyl)-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-ethenyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-(methoxyimino)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(2-acetyl-4-thiazolyl)1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-ethynyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[[[2-(dimethylamino)-ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[(dimethylamino)-methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-4-[2-(7,11-dihydroxy-8,8,10,12-tetramethyl-5,9-dioxo-4,17-dioxabicyclo[14.1.0]heptadecan-3-yl)-1-propenyl]-2-thiazolecarboxylic acid; and

[1S-[1R*,3R*(E),7R*,10S*,11R*,12R*,16S*]]-4-[2-(7,11-dihydroxy-8,8,10,12-tetramethyl-5,9-dioxo-4,17-dioxabicyclo[14.1.0]heptadecan-3-yl)-1-propenyl]-2-thiazolecarboxylic acid methyl ester.

A particularly preferred compound in accordance with the present invention is represented by the formula:

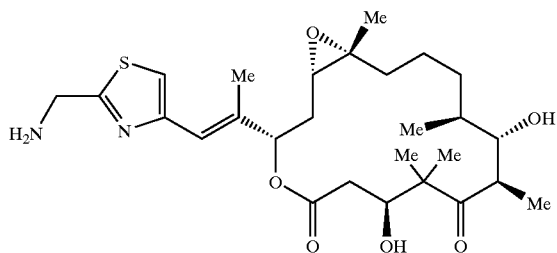

This compound is chemically [1S-[1R*,3R*(E),7R*,10S*,11R*,12R*,16S*]]-7,11-dihydroxy-8,8,10,12,16-pentamethyl-3-[1-methyl-2-(2-aminomethyl-4-thiazolyl)ethenyl]-4,17-dioxabicyclo[14.1.0]heptadecane-5,9-dione.

The epothilone derivatives represented by formula I above, are known compounds. The compounds and a process for their preparation are disclosed in WO 00/50423. Heretofore, however, there has been no recognition that the subject epothilone derivatives would possess activity in the treatment of tumors resistant to treatment with other known chemotherapeutic agents.

The following are definitions of various terms used to describe the compound represented by formula I above.

The term "alkyl" refers to optionally substituted straight- or branched-chain saturated hydrocarbon groups having from 1 to about 20 carbon atoms, preferably from 1 to about 7 carbon atoms. The expression "lower alkyl" refers to optionally substituted alkyl groups having from 1 to about 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., SO$_2$NH$_2$), substituted sulfonamido, nitro, cyano, carboxy, carbamyl (e.g., CONH$_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "alkenyl" refers to optionally substituted unsaturated aliphatic hydrocarbon groups having from 1 to about 9 carbon atoms and one or more double bonds. Substituents may include one or more substituent groups as described above for substituted alkyl.

The term "halogen" or "halo" refers to fluorine, chlorine, bromine and iodine.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having from about 6 to about 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocylooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to about 3 rings and 3 to about 7 carbon atoms per ring, which may be further fused with an unsaturated C$_3$–C$_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4- to 7-membered monocyclic, 7- to 11-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula I in an equivalent amount of the acid in a medium in which the salt precipitates or in an aqueous medium followed by evaporation.

In addition, zwitterions ("inner salts") can be formed and are included within the term "salts" as used herein. Further, solvates and hydrates of the compounds represented by formula I are also included herein.

The compounds represented by formula I above may exist as multiple optical, geometric, and stereoisomers. While the compounds shown herein are depicted for one optical orientation, included within the present invention are all isomers and mixtures thereof.

It is recognized that the compounds represented by formula I above are microtubule-stabilizing agents. Therefore, they are useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The foregoing indications are given herein since it cannot be certain which of the named types of tumors, and others as well, may demonstrate resistance to oncology therapy. "Oncology therapy" refers to treatment of cancer of tumors with chemotherapeutic agents that exert a cytotoxic effect in cells. An example of chemotherapeutic agent is an oncology agent of the taxane family of compounds. It is known, for example, that a considerable number of patients initially responsive to oncology therapy with taxane compounds develop resistance over a course of therapy and that not all cancers respond to treatment with taxane therapy as is the case with virtually all oncology agents. Further, certain diseases, such as colorectal cancers or melanoma, are known to be innately resistant to taxane therapy.

The subject epothilone compounds are highly potent cytotoxic agents capable of killing cancer cells at low nanometer concentrations and are approximately twice as potent as paclitaxel in inducing tubulin polymerization. More important, the subject compounds seem to possess the capacity to retain their antineoplastic activity against human cancers that are naturally insensitive to paclitaxel or have developed resistance to it, both in vitro and in vivo.

Tumors for which the subject epothilone compounds have demonstrated significant antitumor activity include, without intended limitation the following:

[1] Paclitaxel-resistant—HCT116/VM46 colorectal (multidrug resistant, MDR), Pat-21 breast and Pat-7 ovarian carcinoma (clinical isolates, mechanisms of resistance not fully known), A2780Tax ovarian carcinoma (tubulin mutation);

[2] Paclitaxel-insensitive—Pat-26 human pancreatic carcinoma (clinical isolate) and M5076 murine fibrosarcoma; and

[3] Paclitaxel sensitive—A2780 ovarian, LS174T and HCT human colon carcinoma.

In addition, the compounds represented by formula I have demonstrated that they are orally efficacious versus preclinical human tumor xenografts grown in immunocompromized mice or rats. Being efficacious upon oral administration is considered a significant advantage of the subject epothilone derivatives.

The present invention thus provides a method of treating a subject, preferably mammals and especially humans, in need of treatment for a tumor that has demonstrated resistance to therapy with the taxane family of oncologic agents, comprising administering to the subject one of the epothilone compounds represented by formula I in an amount effective for such treatment. Other therapeutic agents such as those described below may be employed with the subject epothilone compounds in their usual dosages. Such agents may be administered prior to, simultaneously with or following the subject epothilone compounds.

An effective amount of the epothilone compounds represented by formula I may be determined by one of ordinary skill in the art, and includes exemplary dosage amounts for a human of from about 0.05 to about 200 mg/kg/day. This dosage is typically administered in a single dose, but can be given in divided doses since the subject compounds are advantageously efficacious via oral administration. The compounds may be administered in a frequent regimen, e.g., every two days for five doses, or intermittently, e.g., every four days for three doses or every eight days for three doses. It will be understood that the specific dose level and frequency of administration for a given subject may be varied and will depend upon a variety of factors including the subject's age, body weight, general health, sex, diet and the like, the mode of administration if not oral, severity of the condition and the like.

The compounds represented by formula I are administered in pharmaceutical compositions containing an amount thereof effective for cancer therapy, and a pharmaceutically acceptable carrier. Such compositions may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation and/or called for by accepted pharmaceutical practice.

The compounds represented by formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The subject compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The subject compounds may also be administered liposomally.

Suitable dosage forms for the subject epothilone derivatives include, without intended limitation, a orally effective composition such as a tablet, capsule, solution or suspension containing about 5 to about 500 mg per unit dosage of a compound represented by formula I or a topical form (about 0.01% to about 5% by weight compound represented by formula I, one to five treatments per day). They may be compounded in a conventional manner with a physiologically acceptable vehicle or carrier, excipient, binder, preservative, stabilizer, flavor, etc., or with a topical carrier.

The compounds represented by formula I can also be formulated in compositions such as sterile solutions or suspensions for parenteral administration. About 0.1 mg to about 500 mg of a compound represented by formula I may be compounded with a physiologically acceptable vehicle, carrier, excipient, binder preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms that may be used. Exemplary compositions include those formulating the present compound(s) with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic acid copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parentally acceptable diluents or solvents, such as Cremophor® (polyoxyethylated caster oil surfactant), mannitol, 1,3-butanediol, water, Ringer's solution, Lactated Ringer's solution, an isotonic sodium chloride solution, or other suitable dispersing or wetting and suspending agents, including synthetic mono- or diglycerides, and fatty acids, including oleic acid. Exemplary compositions for rectal administration include suppositories which may contain, for example, a suitable non-irritating excipient, such as cocoa butter, synthetic glyceride esters or polyethylene glycols, which are solid at ordinary temperature, but liquefy and/or dissolve in the rectal cavity to release the drug.

The compounds of the invention may be administered either alone or in combination with other chemotherapeutic agents or anti-cancer and cytotoxic agents and/or treatments useful in the treatment of cancer or other proliferative diseases. Especially useful are anti-cancer and cytotoxic drug combinations wherein the second drug chosen acts in a different manner or different phase of the cell cycle, e.g. S phase, than the present compounds represented by formula I which exert their effects at the $G_2$-M phase. Example classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; and epothilones A–F or their analogs or derivatives; plant-derived products, such as vinca alkaloids, epipodophyllotoxins, and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The subject compounds may also be used in conjunction with radiation therapy.

The compounds represented by formula I may also be formulated or co-administered with other therapeutic agents that are selected for their particular usefulness in administering therapies associated with the aforementioned conditions. For example, the compounds of the invention may be formulated with agents to prevent nausea, hypersensitivity, and gastric irritation, such as antiemetics, and $H_1$ and $H_2$ antihistaminics.

The above therapeutic agents, when employed in combination with the compounds of the present invention, may be used in those amounts indicated in the Physicians' Desk Reference (PDR) or as otherwise determined by one of ordinary skill in the art.

The following example is given without any intended limitation to further illustrate the invention.

EXAMPLE

[1S-[1R*,3R*(E),7R*,10S*,11R*,12R*,16S*]]-7,11-dihydroxy-8,8,10,12,16-pentamethyl-3-[1-methyl-2-(2-aminomethyl-4-thiazolyl)ethenyl]-4,17-dioxabicyclo[14.1.0]heptadecane-5,9-dione (BMS-310705).

For administration to rodents, the subject compound was administered in either 1:9 ethanol/water, or 1:1:8 Cremophor®/ethanol/water. Final dilution for parenteral administration was made with water one hour before administration. Final dilution for oral administration was made with 0.25 M sodium phosphate buffer (pH 8.0). Paclitaxel was dissolved in a 50/50 mixture of ethanol and Cremophor® and maintained at 4° C. Final dilution was made immediately prior to injection to prevent undesirable precipitation.

Tumor Cell Lines: HCT 116 human carcinoma and HCT116/V/M46 cells were maintained on McCoy's medium and 10% heat-inactivated fetal bovine serum. A2780 human ovarian carcinoma cells and A2780Tax cells were maintained in IMEM and 10% heat-inactivated fetal bovine serum. This paclitaxel resistant cell line does not overexpress P-glycoprotein but has point mutations in the M40 isotype of beta-tubulin 2. Purified tubulin isolated from these resistant cells is refractory to polymerization by paclitaxel and is thought to account for the resistance to this drug, and collateral sensitivity to microtubule depolymerizing agents, such as vinblastine. All other cell lines were maintained in RPM11640 medium with 10% heat-inactivated fetal bovine serum.

Cytotoxicity Assay: the in vivo cytotoxicity was assessed in tumor cells by a tetrazolium-based calorimetric assay at 492 nm. The cells were seeded 24 h prior to drug addition. The reagents were added following a 72 h incubation with serially diluted test compound. Measurements were taken after a further three hours incubation. The results are expressed as median cytotoxic concentration ($IC_{50}$ values).

Clonogenic Cell Colony-Formation Assay: the potency required for the test compound and paclitaxel to kill clonogenic tumor cells (cells that are able to divide indefinitely to form a colony) in vitro was evaluated by a colony formation assay. The concentration needed to kill 90% of clonogenic cancer cells ($IC_{90}$) was determined.

Tubulin Polymerization Assay: the potency required for the test compound and paclitaxel to polymerize tubulin isolated from calf brain was evaluated by published techniques. The effective concentration ($EC_{0.01}$) was defined as the interpolated concentration capable of inducing an initial slope of optical density (OD) of 0.01 OD/minute rate and is calculated using the formula: $EC_{0.01}$=concentration/slope. $EC_{0.01}$ values are expressed as the mean with standard deviation obtained from 3 different concentrations.

In Vivo Antitumor Testing: The following human tumors were utilized: ovarian A2780, ovarian A2780Tax and Pat-7 (established from an ovarian tumor biopsy from a patient who had developed resistance to paclitaxel); and Pat-26 pancreatic carcinoma (from a liver metastasis biopsy). The human tumor xenografts were maintained in Balb/c nu/nu nude mice. Tumors were propagated as subcutaneous transplants in the appropriate mouse strain using tumor fragments obtained from donor mice. All tumor implants for efficacy testing were subcutaneous (sc). The required number of animals needed to detect a meaningful response (6–8) were pooled at the start of the experiment and each was given a subcutaneous implant of a tumor fragment (~50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2–Wt1) provided a measure of treatment-related toxicity.

Tumor response was determined by measurement of tumors with a caliper twice a week until the tumors reached a predetermined "target" size of 0.5 or 1.0 g. Tumor weights (mg) were estimated from the formula:

$$\text{Tumor weight}=(\text{length}\times\text{width}^2)\div 2$$

The maximum tolerated dose (MTD) is defined as the dose level immediately above which excessive toxicity (i.e. more than one death) occurred. The MTD was frequently equivalent to the optimal dose (OD). Activity is described at the OD. Treated mice expiring prior to having their tumors reach target size were considered to have expired from drug toxicity. No control mice expired bearing tumors less than target size. Treatment groups with more than one death caused by drug toxicity were considered to have had excessively toxic treatments and their data were not included in the evaluation of the antitumor efficacy of a compound.

Tumor response end-point was expressed in terms of tumor growth delay (T–C value), defined as the difference in time (days) required for the treated tumors (T) to reach a predetermined target size compared to those of the control group (C). A tumor is defined as "cured" when there is no detectable disease at the time of study termination; the interval between study termination and the end of drug treatment always exceeded 10 times the tumor volume doubling time. Group sizes typically consisted of eight mice in all treatment and control groups. Statistical analyses of response data were carried out using the Gehan's generalized Wilcoxon test.

Cytotoxicity Against Cancer Cells in vitro: as shown in FIG. 1, the results demonstrate that the test compound has a broad spectrum of activity against a panel of tumor cell lines in vitro. Of the 8 cells lines tested, 7 have $IC_{50}$ values in the range of 0.9 nM to 3.5 nM. The highly multi-drug resistant (MDR) colon tumor lines HCT/NVM46 had an $IC_{50}$ value of 11.9 It should be noted that the test drug did substantially overcome the MDR in these cells. This can be seen when it is considered that the ratio of concentration (R/S or resistance ratio) required for paclitaxel to inhibit cell growth by 50% in the resistant cell line vs. the sensitive HCT 116 cell line was 155 fold whereas, in comparison, the ratio for the test drug was only 12.8.

Mechanism of Cytotoxicity—Tubulin Polymerization: The cytotoxic activities of the epothilones, like those of the taxanes, have been linked to stabilization of microtubules, which results in mitotic arrest at the G2/M transition. In this regard, the potency of the test compound was about 2.5-fold more potent than paclitaxel. The tubulin polymerization potency of 4 epothilone compounds is shown in Table 1 below.

TABLE 1

Tubulin Polymerization Potency of Four Epothilones Relative to Paclitaxel

| Analog | Polymerization Potency, $EC_{0.01}$ ($\mu$M) | Ratio of Polymerization Potency of Analog/Paclitaxel |
|---|---|---|
| BMS-310705 | 7.4 | 1.7 |
| BMS-247550 | 3.5 | 0.4 |
| BMS-212188 (Epothilone A) | 2.0 | 0.4 |
| BMS-205535 (Epothilone B) | 1.8 | 0.3 |

Figure 5:
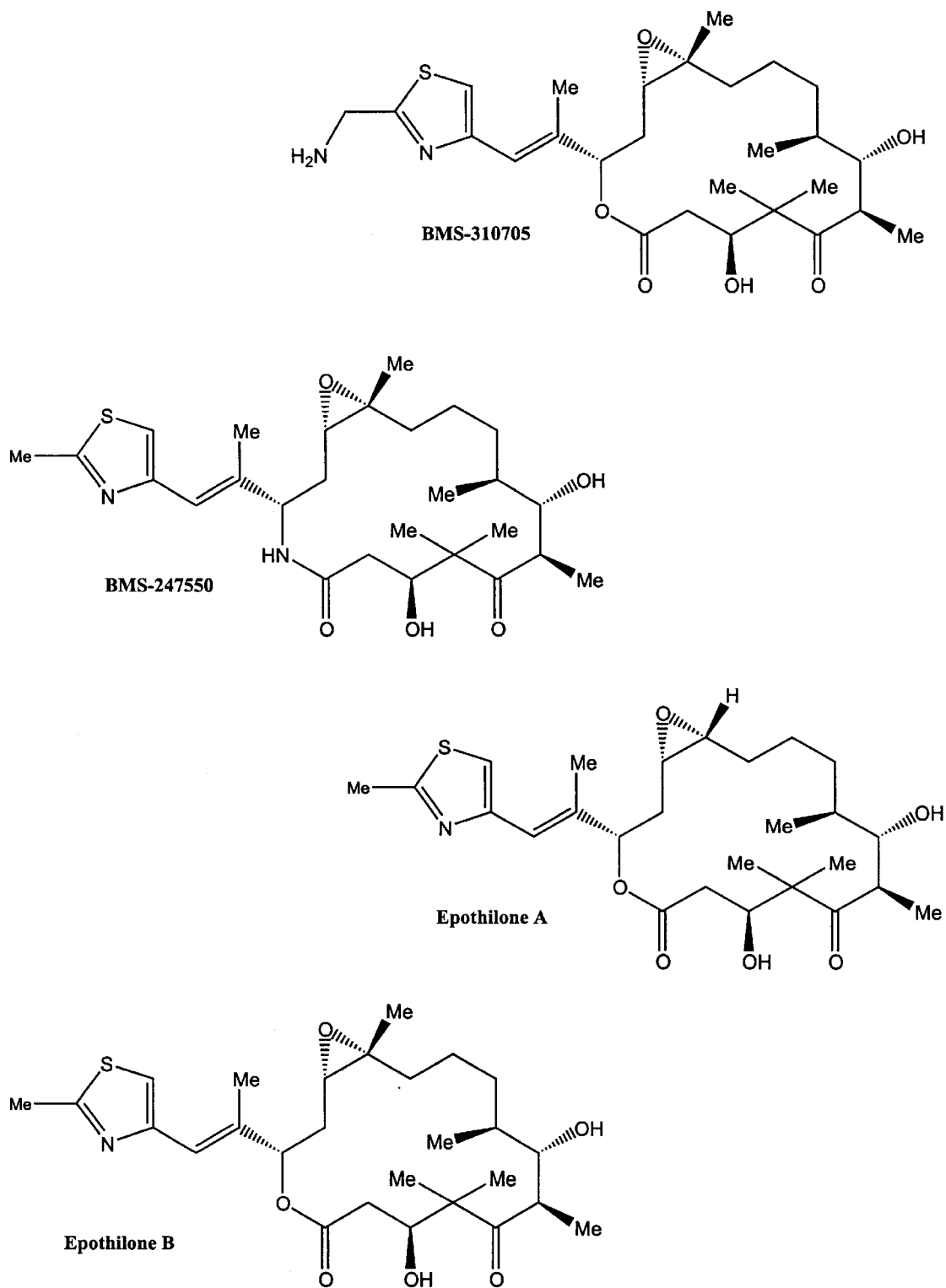
FIG. 5 shows structures of several epothilone analogs.

Structures of the analogs included in Table 1 are shown in FIG. 5.

Figure 2:
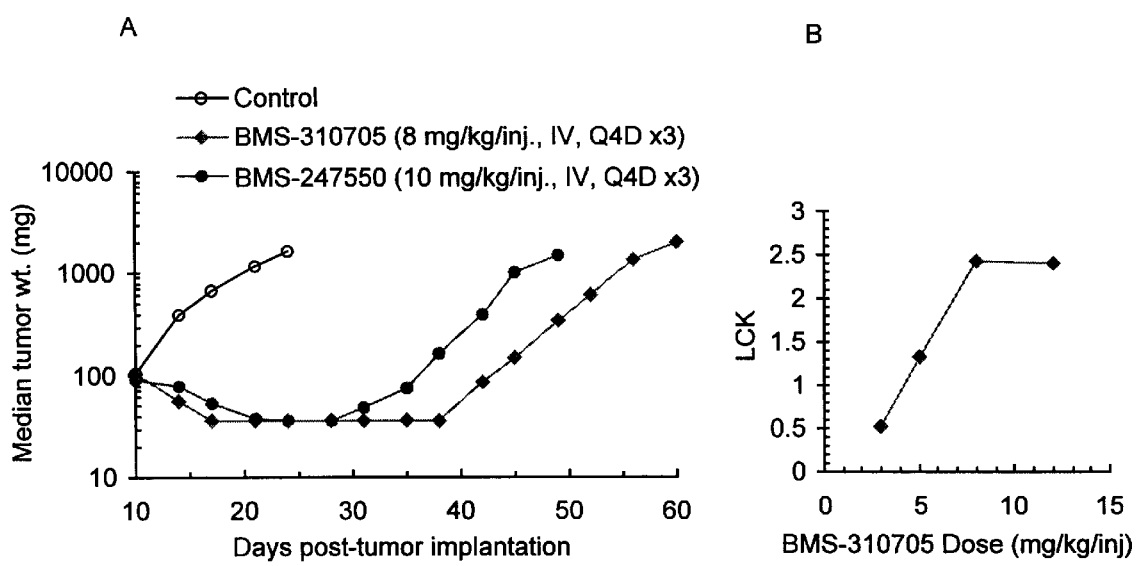
FIG. 2(A) is a graph showing comparative antitumor activity of two epothilone derivatives in Pat-7 human ovarian carcinoma cells.
FIG. 2(B) is a graph showing the dose-response relationship for a compound of the invention.
Figure 3:
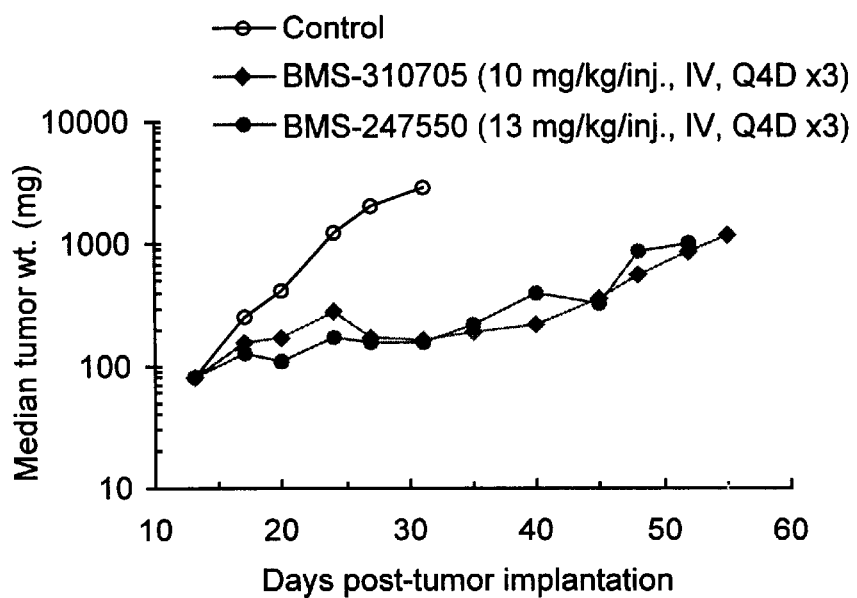
FIG. 3 is a graph showing comparative antitumor activity of two epothilone derivatives in A2780Tax human ovarian carcinoma cells.

Antitumor Activity by Parenteral Administration: the test compound was evaluated in a panel of five human tumor xenografts chosen because of their known, well-characterized resistance to paclitaxel. The tumor models (shown in Table 2 below) were as follows: clinically-derived paclitaxel resistant Pat-7 ovarian carcinoma; A2780Tax ovarian carcinoma xenograft (mutated tubulin); HCT116/VM46 human colon carcinoma xenograft—multidrug resistant (MDR); clinically-derived paclitaxel-resistant Pat-21 breast carcinoma model; and Pat-26 human pancreatic carcinoma model. The subject compound tested retained its antineoplastic activity and was significantly more active than paclitaxel. These results are shown in FIGS. 2 and 3, and in Table 3.

TABLE 2

Tumor Model Characteristics

| Tumor | Histology | Paclitaxel sensitivity | Resistance Mechanism(s) |
|---|---|---|---|
| Human | | | |
| Pat-7 | Ovarian | Resistant[1] | MDR, MRP[2] |
| A2780Tax | Ovarian | Resistant | Tubulin mutation |
| HCT116/VM46 | Colon | Resistant | MDR |
| Pat-21 | Breast | Resistant[1] | Unknown |
| Pat-26 | Pancreatic | Refractory | Unknown |

[1]Clinical resistance to TAXOL
[2]MRP = multidrug resistance related protein

TABLE 3

Preclinical Antitumor Activity of BMS-310705 and Paclitaxel Versus Paclitaxel Resistant Tumors

| | | | BMS-310705 | | BMS-247550 | PACLITAXEL[3] |
|---|---|---|---|---|---|---|
| Tumor | Expt. No. | Rt., schedule | $OD^1$ (mg/kg) | $LCK^2$ | $LCK^2$ | $LCK^2$ |
| Human tumors-in nude mice | | | | | | |
| Pat-7 | 14 | IV, q4dx3 | 8 | 2.4 | 1.8 | 0.8 |
| A2780Tax | 13 | IV, q4dx3 | 10 | 3.6 | 3.5 | 0.8 |
| HCTVM46 | 40 | IV, q4dx3 | 7.5 | 1.5 | 1.3 | 0.55 |
| Pat-21 | 717 | IV, q4dx3;37,66 | 9 | >4.1 | 3.9 | 0.3 |
| Pat-26 | 968 | IV, q4dx3 | 10 | 1.2 | (1.2) | 0.4 |

[1]OD, optimal dose or maximum tolerated dose (MTD).
[2]LCK, gross log cell kill, are for MTD, or highest dose tested if inactive.
[3]Results for paclitaxel were obtained in separate studies A formulation experiment was conducted to note the effect of the vehicle utilized. Since the test compound is stable and highly water-soluble, the effect of a simple solution was compared to the same concentration of test drug in the Cremphor®/ethanol/water vehicle described above. No difference was noted.

Figure 4:
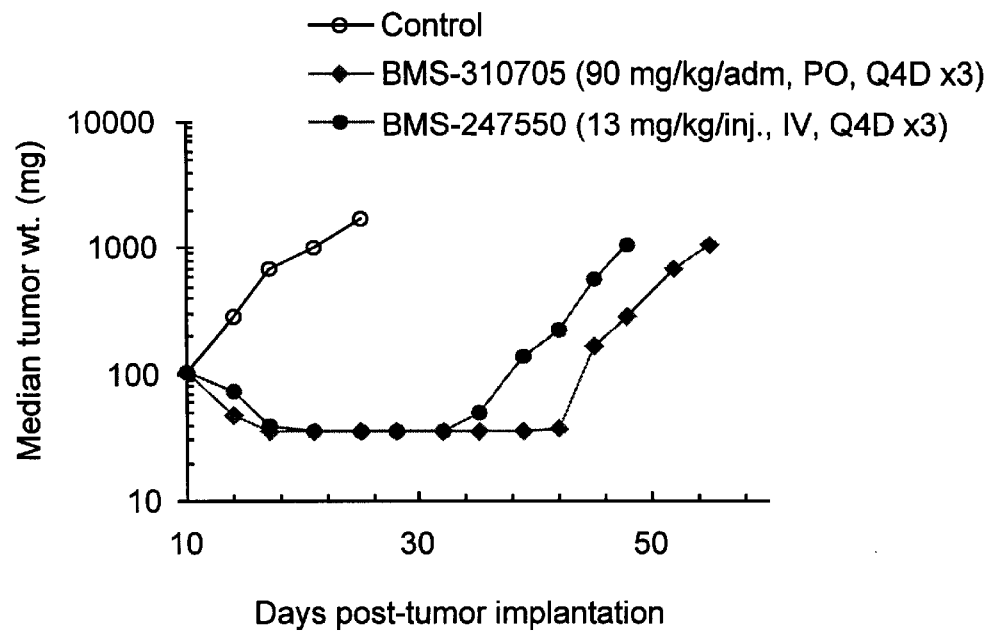
FIG. 4 is a graph showing comparative antitumor activity of an oral epothilone derivative and an IV epothilone derivative in Pat-7 human ovarian carcinoma cells.

Antitumor activity by Oral Route of Administration: as the test compound is more stable at neutral pH than at low pH, the evaluation thereof by oral administration (PO) utilized a pH-buffering vehicle (0.25M potassium phosphate, pH 8.0). As shown in FIG. 4, using an every 4 days×3 schedule, the test compound was highly active orally against the Pat-7 human ovarian carcinoma model. As shown in Table 4 below, the orally administered test compound yielded 2.4 LCK at its MTD. A comparison could not be conducted with Paclitaxel since it is typically inactive when administered by the oral route.

TABLE 4

Antitumor Activity of Oral BMS-310705 and IV BMS-247550

| Tumor | Expt. No. | Rt., schedule | BMS-310705 (PO) OD[1] (mg/kg) | LCK[2] (cures/total) | BMS-247550 LCK[2] |
|---|---|---|---|---|---|
| Pat-7 | 18 | PO, q4dx3 | 90 | 2.4 | 1.9 |

[1]OD, optimal dose or maximum tolerated dose (MTD).
[2]LCK, gross log cell kill.

From the foregoing in vitro experimental evidence, it can be seen that the test compound retains its antineoplastic activity in cancer cells that have developed resistance to paclitaxel, whether through overexpression of the MDR P-glycoprotein or tubulin mutation. From the in vivo evidence, the test compound has clearly demonstrated antitumor activity in all five paclitaxel-resistant tumors evaluated in this study.

A further advantage of the test compound over the prototypical taxanes is its efficacy by oral administration, producing antitumor activity when given orally that is equivalent to that produced by IV drug administration.

What is claimed is:

1. A method of treating a tumor in a mammal, said tumor having demonstrated resistance to oncology therapy and sensitive to compounds of Formula I, comprising administering to said mammal an effective amount of a composition comprising a pharmaceutically acceptable carrier and an epothilone compound of formula I:

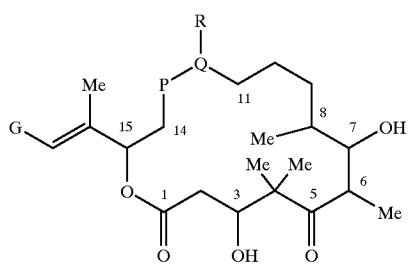

wherein:

P—Q is a carbon-carbon double bond or an epoxide;

G is

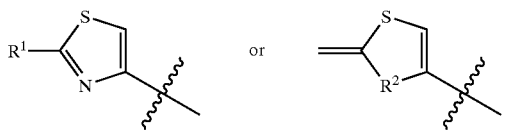

R is selected from the group of H, alkyl, and substituted alkyl;

$R^1$ selected from the group consisting of

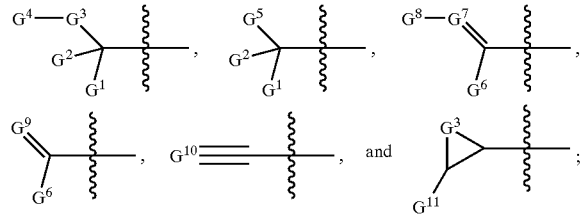

$R^2$ is

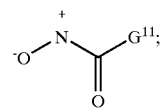

$G^1$ is selected from the group consisting of H, halogen, CN, alkyl and substituted alkyl;

$G^2$ is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2C=O$, $Z^4SO_2$, and optionally substituted glycosyl;

$G^5$ is selected from the group consisting of halogen, $N_3$, NCS, SH, CN, NC, $N(Z^1)_3^+$ and heteroaryl, provided that if $G^1$ and $G^2$ are both hydrogen, $G^5$ is not halogen;

$G^6$ is selected from the group consisting of H, alkyl, substituted alkyl, $CF_3$, $OZ^5$, $SZ^5$, and $NZ^5Z^6$;

$G^7$ is $CZ^7$ or N;

$G^8$ is selected from the group consisting of H, halogen, alkyl, substituted alkyl, $OZ^{10}$, $SZ^{10}$, $NZ^{10}Z^{11}$;

$G^9$ is selected from the group consisting of O, S, —NH— NH— and —N=N—;

$G^{10}$ is N or $CZ^{12}$;

$G^{11}$ is selected from the group consisting of $H_2N$, substituted $H_2N$, alkyl, substituted alkyl, aryl, and substituted aryl;

each $Z^1$, $Z^6$, $Z^9$, and $Z^{11}$ is, independently, selected from the group consisting of H, alkyl, substituted alkyl, acyl, and substituted acyl;

$Z^2$ is selected from the group consisting of H, alkyl, substituted alkyl, aryl, substituted aryl, and heterocycle;

each $Z^3$, $Z^5$, $Z^8$, and $Z^{10}$ is, independently, selected from the group consisting of H, alkyl, substituted alkyl, acyl, substituted acyl, aryl, and substituted aryl;

$Z^4$ is selected from the group consisting of alkyl, substituted alkyl, aryl, substituted aryl, and heterocycle;

$Z^7$ is selected from the group consisting of H, halogen, alkyl, substituted alkyl, aryl, substituted aryl, $OZ^8$, $SZ^8$, and NZ$^8$Z$^9$, provided that if G$^6$ and G$^8$ are both H, then Z$^7$ is not also H; and Z$^{12}$ is selected from the group consisting of H, halogen, alkyl, substituted alkyl, aryl, and substituted aryl;

with the proviso that when R$^1$ is

G$^1$, G$^2$, G$^3$ and G$^4$ cannot simultaneously have the following meanings:
G$^1$ and G$^2$ are H, G$^3$ is O, and G$^4$ is H or Z$^2$C=O wherein Z$^2$ is an alkyl group, and pharmaceutically acceptable salts thereof and any hydrates, solvates or geometric, optical and stereoisomers thereof.

2. The method of claim 1 wherein said compound is of formula Ia:

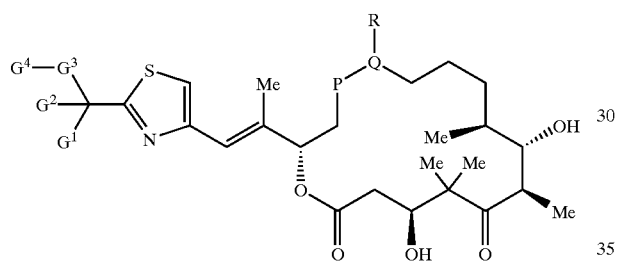

wherein:

P—Q is a carbon-carbon double bond or an epoxide;

R is H or a methyl group;

G$^1$ is H, an alkyl group, a substituted alkyl group or a halogen atom;

G$^2$ is H, an alkyl group or a substituted alkyl group;

G$^3$ is an O atom, an S atom or an NZ$^1$ group;

Z$^1$ is H, an alkyl group, a substituted alkyl group, an acyl group, or a substituted acyl group;

G$^4$ is H, an alkyl group, a substituted alkyl group, an OZ$^2$ group, an NZ$^2$Z$^3$ group, +Z$^2$C=O group, a Z$^4$SO$_2$ group or an optionally substituted glycosyl group;

Z$^2$ is H, an alkyl group, a substituted alkyl group, an aryl group, a substituted aryl group or a heterocyclic group;

Z$^3$ is H, an alkyl group, a substituted alkyl group, an acyl group or a substituted acyl group; and Z$^4$ is alkyl, a substituted alkyl, an aryl, a substituted aryl or a heterocyclic group;

with the proviso that G$^1$, G$^2$, G$^3$ and G$^4$ cannot simultaneously have the following meanings:
G$^1$ and G$^2$ are H, G$^3$ is O, and G$^4$ is H or Z$^2$C=O wherein Z$^2$ is an alkyl group.

3. The method of claim 1 wherein said compound is of formula Ib:

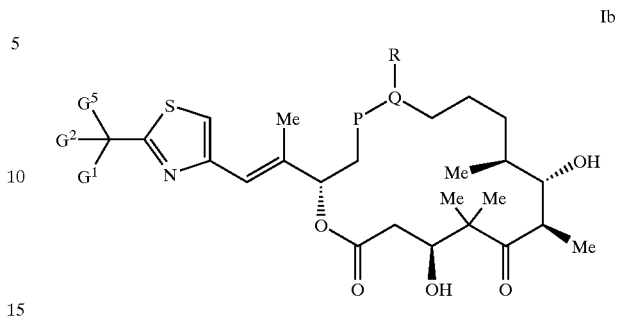

wherein:

P—Q is a carbon-carbon double bond or an epoxide;

R is H or a methyl group;

G$^1$ is H, an alkyl group, a substituted alkyl group or a halogen atom;

G$^2$ is H, an alkyl group or a substituted alkyl group; and

G$^5$ is an N$_3$ group, an NCS group, an SH group, a CN group, an NC group or a heterocyclic group.

4. The method of claim 1 wherein said compound is of formula IIa:

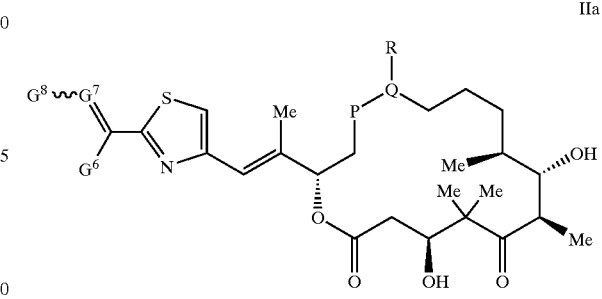

wherein:

P—Q is a carbon-carbon double bond or an epoxide;

R is H or a methyl group;

G$^6$ is H, an alkyl group, a substituted alkyl group or a CF$_3$, OZ$^5$, SZ$^5$ or NZ$^5$Z$^6$ group;

Z$^5$ is H, an alkyl group, a substituted alkyl group, an acyl group or a substituted acyl group;

Z$^6$ is H, an alkyl group or a substituted alkyl group;

G$^7$ is a CZ$^7$ group or a N atom;

Z$^7$ is H, halogen atom, an alkyl group, a substituted alkyl group, an aryl group, or a substituted aryl group, or an OZ$^8$, SZ$^8$ or NZ$^8$Z$^9$ group;

Z$^8$ is H, an alkyl group, a substituted alkyl group, an acyl group or a substituted acyl group;

Z$^9$ is H, an alkyl group or a substituted alkyl group;

G$^8$ is H, a halogen atom, an alkyl group, a substituted alkyl group or an OZ$^{10}$, SZ$^{10}$ or NZ$^{10}$Z$^{11}$ group, provided that G$^6$, G$^8$ and Z$^7$ are not all H;

Z$^{10}$ is H, an alkyl group, a substituted alkyl group, an acyl group, a substituted acyl group, an aryl group, or a substituted aryl group; and Z$^{11}$ is H, an alkyl group, a substituted alkyl group, an acyl group, or a substituted acyl group.

5. The method of claim 1 wherein said compound is of formula IIb:

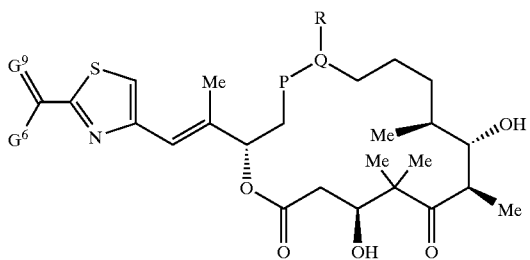

wherein:
P—Q is a carbon-carbon double bond or an epoxide;
R is H or a methyl group;
$G^6$ is H, an alkyl group, a substituted alkyl group or a $CF_3$, $OZ^5$, $SZ^5$ or $NZ^5Z^6$ group;
$Z^5$ is H, an alkyl group, a substituted alkyl group, an acyl group or a substituted acyl group;
$Z^6$ is H, an alkyl group or a substituted alkyl group; and
$G^9$ is O, S or an —N=N— group.

6. The method of claim 1 wherein said compound is of formula III:

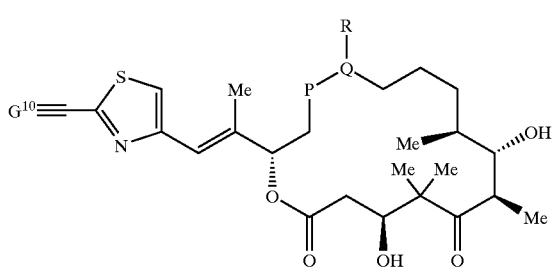

wherein:
P—Q is a carbon-carbon double bond or an epoxide;
R is H or a methyl group;
$G^{10}$ is an N atom or a $CZ^{12}$ group; and
$Z^{12}$ is H, a halogen atom, an alkyl group, a substituted alkyl group, an aryl group, or a substituted aryl group.

7. The method of claim 1 wherein said compound is of formula IV:

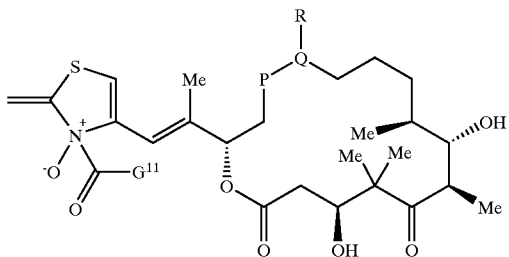

wherein:
P—Q is a carbon-carbon double bond or an epoxide;
R is H or a methyl group; and
$G^{11}$ is an $H_2N$ group, a substituted $H_2N$ group, an alkyl group, a substituted alkyl group, an aryl group or a substituted aryl group.

8. The method of claim 1 wherein said compound is selected from the group consisting of:
[1S-[1R*,3R*(E),7R*,10S*,11R*,12R*,16S*]]-3-[2-[2-(azidomethyl)-4-thiazolyl]-1-methylethenyl]-7,11-dihydroxy-8,8,10,12,16-pentamethyl-4,17-dioxabicyclo-[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-(2-aminomethyl-4-thiazolyl)ethenyl]-4,17-dioxabicyclo[14.1.0]heptadecane-5,9-dione;

[1S-[1R*,3R*(E),7R*,10S*,11R*,12R*,16S*]]-3-[2-[2-[[[(1,1-dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-[[[(1,1-dimethylethoxy)carbonyl]amino]methyl]-4-thiazolyl]-1-methyl-ethenyl]-4,8-dihydroxy-5,5,7,9,13-pentamethyl-1-oxa-13(Z)-cyclohexadecene-2,6-dione;

[4S-[4R*,7S*,8R*,9R*,15R*(E)]]-16-[2-[2-(aminomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(3-acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide;

[1S-[1R*,3R*(E),7R*,10S*,11R*,12R*,16S*]]-7,11-dihydroxy-3-[2-[2-(methoxymethyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-(phenoxymethyl)-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[(ethylthio)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(ethoxymethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(2,3,4,6-tetraacetyl-alpha-glucosyloxy)methyl]-4- thiazolyl]ethenyl]-4,17-dioxabicyclo[14.1.0]
heptadecane-5,9-dione;

[1S-[1R*,3R*(E),7R*,10S*,11R*,12R*,16S*]]-7,11-
dihydroxy-8,8,10,12-tetramethyl-3-[1-methyl-2-[2-
[(2',3',4',6'-tetraacetyl-beta-glucosyloxy)methyl]-4-
thiazolyl]ethenyl]-4,17-dioxabicyclo[14.1.0]
heptadecane-5,9-dione;

[1S-[1R*,3R*(E),7R*,10S*,11R*,12R*,16S*]]-7,11-
dihydroxy-8,8,10,12-tetramethyl-3-[1-methyl-2-[2-
[(6'-acetyl-alpha-glucosyloxy)methyl]-4-thiazolyl]
ethenyl]-4,17-dioxabicyclo[14.1.0]heptadecane-5,9-
dione;

[1S-[1R*,3R*(E),7R*,10S*,11R*,12R*,16S*]]-7,11-
dihydroxy-8,8,10,12,16-pentamethyl-3-[1-methyl-2-
[2-[p-toluenesulfonyloxy)methyl]-4-thiazolyl]
ethenyl]-4,17-dioxabicyclo[14.1.0]heptadecane-5,9-
dione;

[1S-[1R*,3R*(E),7R*,10S*,11R*,12R*,16S*]]-3-[2-[2-
(bromomethyl)-4-thiazolyl]-1-methylethenyl]-7,11-
dihydroxy-8,8,10,12-tetramethyl-4,17-dioxabicyclo
[14.1.0]heptadecane-5,9-dione;

[1S-[1R*,3R*(E),7R*,10S*,11R*,12R*,16S*]]-3-[2-(5-
bromo-2-methyl-4-thiazolyl)-1-methylethenyl]-7,11-
dihydroxy-8,8,10,12-tetramethyl-4,17-dioxabicyclo
[14.1.0]heptadecane-5,9-dione;

[1S-[1R*,3R*(E),7R*,10S*,11R*,12R*,16S*]]-3-[2-[2-
(cyanomethyl)-4-thiazolyl]-1-methylethenyl]-7,11-
dihydroxy-8,8,10,12,16-pentamethyl-4,17-
dioxabicyclo[14.1.0]heptadecane-5,9-dione;

[4S-[4R*,7S*,8R*,9R*,15R*(E)]]-16-[2-[2-
(cyanomethyl)-4-thiazolyl]-1-methylethenyl]-4,8-
dihydroxy-5,5,7,9,13-pentamethyl-1-oxa-13(Z)-
cyclohexadecene-2,6-dione;

[1S-[1R*,3R*(E),7R*,10S*,11R*,12R*,16S*]]-7,11-
dihydroxy-3-[2-[2-(1H-imidazol-1-ylmethyl)-4-
thiazolyl]-1-methylethenyl]-8,8,10,12-pentamethyl-4,
17-dioxabicyclo[14.1.0]heptadecane-5,9-dione;

[1S-[1R*,3R*(E),7R*,10S*,11R*,12R*,16S*]]-3-[2-(2-
formyl-4-thiazolyl)-1-methylethenyl]-7,11-dihydroxy-
8,8,10,12-tetramethyl-4,17-dioxabicyclo[14.1.0]
heptadecane-5,9-dione;

[1S-[1R*,3R*(E),7R*,10S*,11R*,12R*,16S*]]-3-[2-(2-
formyl-4-thiazolyl)-1-methylethenyl]-7,11-dihydroxy-
8,8,10,12,16-pentamethyl-4,17-dioxabicyclo[14.1.0]
heptadecane-5,9-dione;

[1S-[1R*,3R*(E),7R*,10S*,11R*,12R*,16S*]]-3-[2-(2-
ethenyl-4-thiazolyl)-1-methylethenyl]-7,11-dihydroxy-
8,8,10,12-tetramethyl-4,17-dioxabicyclo[14.1.0]
heptadecane-5,9-dione;

[1S-[1R*,3R*(E),7R*,10S*,11R*,12R*,16S*]]-7,11-
dihydroxy-3-[2-[2-(methoxyimino)-4-thiazolyl]-1-
methylethenyl]-8,8,10,12-tetramethyl-4,17-
dioxabicyclo[14.1.0]heptadecane-5,9-dione;

[1S-[1R*,3R*(E),7R*,10S*,11R*,12R*,16S*]]-7,11-
dihydroxy-8,8,10,12-tetramethyl-3-[1-methyl-2-[2-
[[(phenylmethyl)imino]methyl]-4-thiazolyl]ethenyl]-4,
17-dioxabicyclo[14.1.0]heptadecane-5,9-dione;

[1S-[1R*,3R*(E),7R*,10S*,11R*,12R*,16S*]]-3-[2-(2-
acetyl-4-thiazolyl)-1-methylethenyl]-7,11-dihydroxy-
8,8,10,12-tetramethyl-4,17-dioxabicyclo[14.1.0]
heptadecane-5,9-dione;

[1S-[1R*,3R*(E),7R*,10S*,11R*,12R*,16S*]]-7,11-
dihydroxy-8,8,10,12-tetramethyl-3-[1-methyl-2-(2-
oxiranyl-4-thiazolyl)ethenyl]-4,17-dioxabicyclo
[14.1.0]heptadecane-5,9-dione;

[1S-[1R*,3R*(E),7R*,10S*,11R*,12R*,16S*]]-7,11-
dihydroxy-3-[2-[2-(2-iodoethenyl)-4-thiazolyl]-1-
methylethenyl]-8,8,10,12-tetramethyl-4,17-
dioxabicyclo[14.1.0]heptadecane-5,9-dione;

[1S-[1R*,3R*(E),7R*,10S*,11R*,12R*,16S*]]-3-[2-(2-
ethynyl-4-thiazolyl)-1-thiazolyl)-1-methylethenyl]-7,
11-dihydroxy-8,8,10,12-tetramethyl-4,17-dioxabicyclo
[14.1.0]heptadecane-5,9-dione;

[1S-[1R*,3R*(E),7R*,10S*,11R*,12R*,16S*]]-7,11-
dihydroxy-8,8,10,12,16-pentamethyl-3-[1-methyl-2-
[2-[(methylamino)methyl]-4-thiazolyl]ethenyl]-4,17-
dioxabicyclo[14.1.0]heptadecane-5,9-dione;

[1S-[1R*,3R*(E),7R*,10S*,11R*,12R*,16S*]]-3-[2-[2-
[[[2-(dimethylamino)ethyl]amino]methyl]-4-
thiazolyl]-1-methylethenyl]-7,11-dihydroxy-8,8,10,12,
16-pentamethyl-4,17-dioxabicyclo[14.1.0]
heptadecane-5,9-dione;

[1S-[1R*,3R*(E),7R*,10S*,11R*,12R*,16S*]]-3-[2-[2-
[(dimethylamino)methyl]-4-thiazolyl]-1-
methylethenyl]-7,11-dihydroxy-8,8,10,12,16-
pentamethyl-4,17-dioxabicyclo[14.1.0]heptadecane-5,
9-dione;

[1S-[1R*,3R*(E),7R*,10S*,11R*,12R*,16S*]]-3-[2-[2-
[[bis(2-methoxyethyl)amino]methyl]-4-thiazolyl]-1-
methylethenyl]-7,11-dihydroxy-8,8,10,12,16-
pentamethyl-4,17-dioxabicyclo[14.1.0]heptadecane-5,
9-dione;

[1S-[1R*,3R*(E),7R*,10S*,11R*,12R*,16S*]]-7,11-
dihydroxy-8,8,10,12,16-pentamethyl-3-[1-methyl-2-
[2-[(4-methyl-1-piperazinyl)methyl]-4-thiazolyl]
ethenyl]-4,17-dioxabicyclo[14.1.0]heptadecane-5,9-
dione;

[1S-[1R*,3R*(E),7R*,10S*,11R*,12R*,16S*]]-4-[2-(7,
11-dihydroxy-8,8,10,12-tetramethyl-5,9-dioxo-4,17-
dioxabicyclo[14.1.0]heptadecan-3-yl)-1-propenyl]-2-
thiazolecarboxylic acid; and

[1S-[1R*,3R*(E),7R*,10S*,11R*,12R*,16S*]]-4-[2-(7,
11-dihydroxy-8,8,10,12-tetramethyl-5,9-dioxo-4,17-
dioxabicyclo[14.1.0]heptadecan-3-yl)-1-propenyl]-2-
thiazolecarboxylic acid methyl ester.

9. The method of claim 8 wherein said compound is
[1S-[1R*,3R*(E),7R*,10S*,11R*,12R*,16S*]]-7,11-
dihydroxy-8,8,10,12,16-pentamethyl-3-[1-methyl-2-
(2-aminomethyl-4-thiazolyl)ethenyl]-4,17-
dioxabicyclo[14.1.0]heptadecane-5,9-dione.

10. The method of claim 1 wherein said epothilone
compound is of formula:

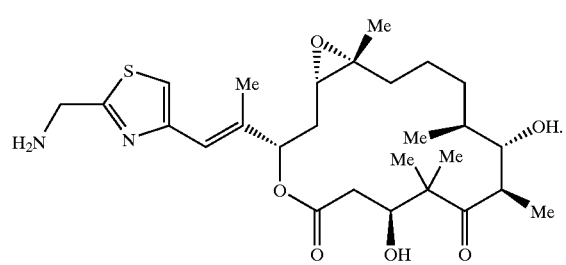

11. The method of claim 1 wherein said mammal is a human.

12. The method of claim 1 wherein the composition containing said epothilone compound is administered parenterally.

13. The method of claim 12 wherein said epothilone compound is of formula:

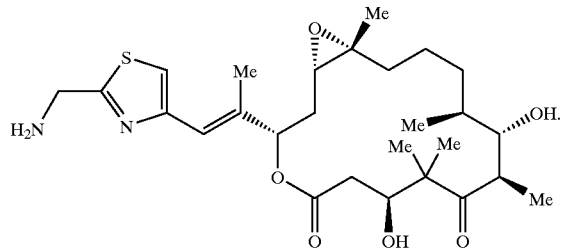

14. The method of claim 1 wherein the composition containing said epothilone compound is administered orally.

15. The method of claim 14 wherein said epothilone compound is of formula:

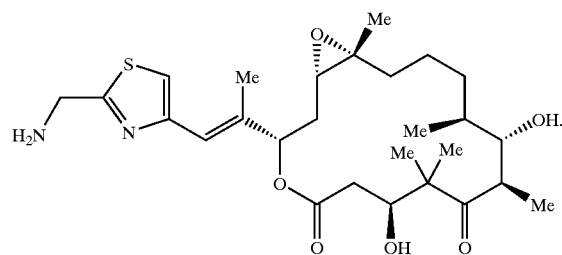

16. The method of claim 1 wherein said tumor was initially not responsive to oncology therapy.

17. The method of claim 1 wherein said tumor was initially responsive to oncology therapy, but developed resistance thereto during the course of treatment.

18. The method of claim 1 wherein said compound is administered simultaneously or sequentially with a chemotherapeutic agent useful in the treatment of cancer or other proliferative diseases.

19. The method of claim 1 wherein said tumor was initially not responsive to oncology taxane therapy.

20. The method of claim 1 wherein said tumor was initially responsive to oncology taxane therapy but developed resistance thereto during the course of treatment.

* * * * *